United States Patent [19]

Yu

[11] 4,199,508

[45] Apr. 22, 1980

[54] 2-(5-P-CHLOROPHENYL-2-FURYL)-5-METHYL-1,3,4-OXADIAZOLE

[75] Inventor: Chia-Nien Yu, Norwich, N.Y.

[73] Assignee: Morton-Norwich Products, Inc., Norwich, N.Y.

[21] Appl. No.: 13,055

[22] Filed: Feb. 21, 1979

[51] Int. Cl.$^2$ .......................................... C07D 271/10
[52] U.S. Cl. .................................... 548/143; 424/272
[58] Field of Search .................................... 260/307 G

[56] References Cited

U.S. PATENT DOCUMENTS 4,134,893  1/1979  Yu ..................... 260/307 G

*Primary Examiner*—Anton H. Sutto
*Attorney, Agent, or Firm*—Anthony J. Franze

[57] ABSTRACT

2-(5-p-Chlorophenyl-2-furyl)-5-methyl-1,3,4-oxadiazole is useful as an anti-inflammatory agent.

1 Claim, No Drawings

2-(5-P-CHLOROPHENYL-2-FURYL)-5-METHYL-1,3,4-OXADIAZOLE

This invention is concerned with the chemical compound 2-(5-p-chlorophenyl-2-furyl)-5-methyl-1,3,4-oxadiazole.

This compound possesses pharmacologic activity. In particular, it possesses anti-inflammatory properties as evidenced by its ability to inhibit edema induced in rats by administration of carrageein. Thus, when administered at a dose of 300 mg/kg suspended in a vehicle such as aqueous methyl cellulose per os to rats receiving carrageenin, edema associated with that substance is inhibited.

The method currently preferred for the preparation of the compound of this invention is described as follows:

A. 1-Acetyl-2-(5-p-chlorophenyl-2-furoyl)hydrazine

A mixture of 111.5 g (0.5 mole) of 5-(p-chlorophenyl)furoic acid in 500 ml of thionyl chloride was heated at reflux for 1-1¼ hr. After slight cooling, the reaction mixture was filtered and the filtrate was concentrated in a water bath at reduced pressure to a creamy solid. The solid was dissolved in 400 ml of chloroform. To this chloroform solution under stirring at room temperature was added a suspension of 74 g (1 mole) of acetyl hydrazine in 900 ml of chloroform. Addition was completed in about 20 min. White creamy solid separated fairly readily while the temperature rose to about 45°. The mixture was allowed to stir at ambient temperature overnight.

The mixture was filtered and the solid was washed with chloroform and air dried. The solid was further triturated with water, filtered, washed with water again and air dried. The yield of crude product was 120 g (89%).

Recrystallization from ethyl acetate gave 95 g, m.p. 206°–208°.

Anal. Calcd. for $C_{13}H_{11}ClN_2O_3$: C, 56.02%; H, 3.98%; N, 10.05% Found: C, 55.95%; H, 3.99%; N, 9.99%.

B. 2-(5-p-Chlorophenyl-2-furyl)-5-methyl-1,3,4-oxadiazole

A mixture of 45 g (0.15 mole) of A. in 300 ml of phosphorus oxychloride was heated at reflux for 4 hours. After cooling, the reaction mixture was poured cautiously, with stirring into crushed ice. Solid separated fairly readily. After overnight cooling, the mixture was filtered and the solid was washed well with water and air dried. The yield was 41 g (97%), m.p. 128°–132°.

Two recrystallizations of 2.7 g from alcohol gave a m.p. of 132°–134°.

Anal. Calcd. for $C_{13}H_9ClN_2O_2$: C, 59.89%; H, 3.48%; N, 10.75%. Found: C, 59.90%; H, 3.55%; N, 10.71%.

The compound of this invention is readily composed in a variety of conventional administrable forms such as tablets, dragees, suspensions, capsules, and the like using classic vehicles and adjuvants with which there is no incompatibility.

What is claimed is:

1. The compound 2-(5-p-Chlorophenyl-2-furyl)-5-methyl-1,3,4-oxadiazole.